United States Patent [19]

Riederer et al.

[11] Patent Number: 4,739,026

[45] Date of Patent: * Apr. 19, 1988

[54] CONTINUOUS METHOD FOR ALTERING THE MOLECULAR WEIGHT OF ORGANOSILICON COMPOSITIONS

[75] Inventors: Manfred Riederer, Burghausen; Martin Piehler, Mehring, both of Fed. Rep. of Germany

[73] Assignee: Wacker-Chemie GmbH, Munich, Fed. Rep. of Germany

[*] Notice: The portion of the term of this patent subsequent to Jul. 8, 2003 has been disclaimed.

[21] Appl. No.: 864,233

[22] Filed: May 19, 1986

[30] Foreign Application Priority Data

May 30, 1985 [DE] Fed. Rep. of Germany ....... 3519411

[51] Int. Cl.$^4$ .......................... C07F 7/08; C08G 77/04
[52] U.S. Cl. ...................................... 528/33; 528/15; 528/16; 528/13; 528/14; 528/19; 528/21; 528/23; 556/462; 526/64
[58] Field of Search .................. 528/33, 23, 19, 21, 528/13, 14, 15, 16; 526/64

[56] References Cited

U.S. PATENT DOCUMENTS

| | | | |
|---|---|---|---|
| 3,933,882 | 1/1976 | Lei et al. | 528/15 |
| 4,128,568 | 12/1978 | Büchner et al. | 528/35 |
| 4,250,290 | 2/1981 | Petersen | 528/14 |
| 4,426,508 | 1/1984 | Dromard et al. | 528/23 |
| 4,551,515 | 11/1985 | Herberg et al. | 528/14 |
| 4,599,437 | 7/1986 | Riederer | 528/16 |

*Primary Examiner*—Wilbert J. Briggs, Sr.
*Assistant Examiner*—David W. Woodward

[57] ABSTRACT

A continuous method for altering the molecular weight of organosilicon compositions containing Si-bonded oxygen in the presence of a catalyst and preferably under decreased pressure, in which a cylindrical reactor is employed have a ratio of length to inside diameter of between 1:1 and 50:1. A reactive mixture is stirred in the cylindrical reactor by a stirring apparatus having one or more stirring blades, so that the mixture is subjected to a maximum centrifugal acceleration $b_{max}$ of at least 70 m.s$^{-2}$ and more preferably at least 165 m.s$^{-2}$.

4 Claims, 1 Drawing Sheet

U.S. Patent
Apr. 19, 1988
4,739,026
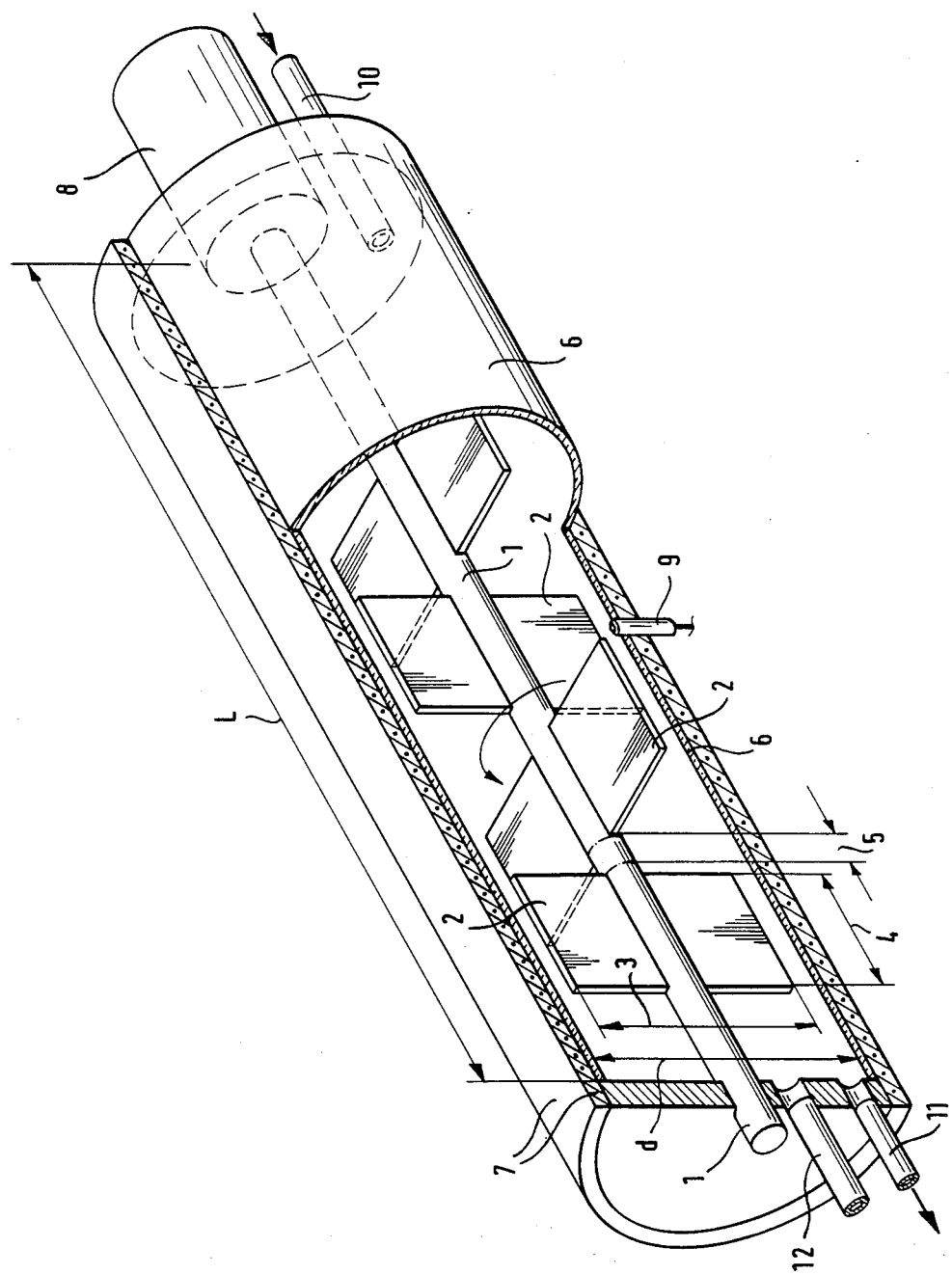

CONTINUOUS METHOD FOR ALTERING THE MOLECULAR WEIGHT OF ORGANOSILICON COMPOSITIONS

The present invention relates to a method for altering the molecular weight of organosilicon compositions and more particularly to a continuous method for altering the molecular weight of organosilicon compositions by reacting organosilicon compositions containing Si-bonded oxygen in the presence of a condensation and/or equilibration catalyst in a reactor in which an annular flow is generated by stirring.

BACKGROUND OF THE INVENTION

A method for altering the molecular weight of organosilicon compositions containing Si-bonded oxygen in the presence of phosphonitrile chloride catalysts is described in U.S. Pat. No. 3,839,388 to Nitzsche et al. In the method described in the above cited patent, a twin screw kneader, such as described in British Pat. No. 1,174,219 (Werner & Pfleiderer), is used as a reactor. Also, U.S. Pat. No. 4,128,568 to Büchner et al describes a continuous process for preparing highly viscous polydiorganosiloxanes, in which substantially cyclic diorganopolysiloxanes are reacted with chain-regulating materials in the presence of alkali catalysts. In the process described therein, the reactor consists of several zones, each of which is provided with stirring or transporting elements which generate countercurrents in two adjacent zones of the reactor.

Therefore, it is an object of the present invention to provide a continuous method for altering the molecular weight of organosilicon compositions containing Si-bonded oxygen without the formation of foam in the reactor. Another object of the present invention is to increase the capacity of the reactor without increasing the size of the reactor. A further object of the present invention is to provide a continuous method for altering the molecular weight of organosilicon compositions having Si-bonded hydrogen and achieve a better space-time-yield ratio.

SUMMARY OF THE INVENTION

The foregoing objects and others which will become apparent from the following description are accomplished in accordance with this invention, generally speaking, by providing a continuous method for modifying the molecular weight of organosilicon compositions containing Si-bonded oxygen which comprises reacting the organosilicon compositions in the presence of a homogeneous catalyst in a cylindrical reactor having a ratio of length to inside diameter of from 1:1 to 50:1, and by stirring the reactive mixture with a stirring mechanism having one or more stirring blades, so that the reactive mixture is subjected to a maximum centrifugal acceleration $b_{max}$ of at least 70 m.s$^{-2}$.

BRIEF DESCRIPTION OF THE DRAWING

The drawing illustrates a reactor which has proven to be especially effective in the method of this invention. In the drawing, the tube-type reactor (6) consists of a glass tube which is equipped with a heating jacket (7). At one end of the reactor is feed line (10) and at the other end is an outlet (11) for the product and a vacuum connection (12) which communicates with a vacuum pump. The center of the tube-type reactor is traversed by a shaft (1), which is driven by an external motor (8). The shaft (1) is equipped with rectangular stirring blades (2) which are staggered at 90° from each other.

DESCRIPTION OF THE INVENTION

In the method of this invention for continuously modifying the molecular weight of organosilicon compositions comprising Si-bonded oxygen, it is possible to use any of the organosilicon compositions comprising Si-bonded oxygen whose molecular weight has been or could have been continuously modified heretofore, such as linear organo(poly)siloxanes of the formula $$AO(SiR_2O)_nA,$$

and cyclic organo(poly)siloxanes having the formula $$(SiR_2O)_{n'}$$

as well as mixtures of linear or cyclic organo(poly)siloxanes or mixtures containing linear and cyclic organo(poly)siloxanes.

In the above formulas, R represents the same or different monovalent hydrocarbon radicals or substituted monovalent hydrocarbon radicals, A represents hydrogen or the —SiR$_3$ group, where R is the same as above and n is an integer having a value of at least 1 and n' is an integer having a value from 3 to 7. Although these formulas do not generally indicate the presence of other groups, up to 5 mol percent of the diorganosiloxane units may be substituted with other siloxane units, such as monoorganosiloxane and/or SiO$_{4/2}$ units. These siloxane units are generally present only as impurities and are generally difficult to remove or avoid.

Examples of monovalent hydrocarbon radicals represented by R are alkyl radicals, such as the methyl, n-butyl and sec-butyl radicals; alkenyl radicals such as the vinyl radical; and aryl radicals, such as the phenyl radical.

Examples of substituted monovalent hydrocarbon radicals represented by R are cyanoalkyl radicals, such as the betacyanoethyl radical; haloalkyl radicals, such as the 3,3,3-trifluoropropyl radical and haloaryl radicals, such as the o-, m- and p-chlorophenyl radicals.

It is preferred that at least 80 percent of the number of R radicals be methyl radicals because they are readily available. Such other R radicals as may be present are preferably vinyl and/or phenyl radicals.

The viscosity of the organopolysiloxanes used in the method of this invention is preferably in the range of from 10 to 1,000 mPa.s at 25° C. Organopolysiloxanes having this viscosity and corresponding to the above formulas where A is generally hydrogen, are generally obtained directly from the hydrolysis of the corresponding organochlorosilanes, especially dimethyldichlorosilane.

The definition of R above also applies to the SiC-bonded organic radicals of the other organosilicon compositions, which may be used in this invention.

It is also possible to use branched organo(poly)siloxanes in the method of this invention. However, if the product obtained by this method is to be used to prepare elastomers, it is preferred that a (poly)siloxane chain which is essentially free of branching be used in this method for modifying the molecular weight of the organosilicon compositions employed.

The reaction involved in the continuous alteration of the molecular weight of organosilicon compositions comprising Si-bonded oxygen can be accelerated by catalysts. Such catalysts are generally substances, which according to the definition of Bronstedt or Lewis, can be described as acids or bases. Since it is difficult to remove undissolved solids from highly viscous oils, the method of this invention is limited to homogeneous catalysts and to catalysts, which following deactivation, are soluble in the reactive mixture. Homogeneous catalysts are preferred. Examples of such acid catalysts are protonic acids such as sulfuric acid, chlorosulfonic acid, selenic acid, nitric acid, phosphoric acids, boric acid, Lewis acids such as ferric(III)-chloride, ferric(III)-chloride-hexahydrate, aluminum chloride, boron trifluoride, zinc chloride and tin(IV)-chloride, as well as phosphonitrile chloride, aluminum sulfate, or mixtures of two or more of these substances.

Examples of basic catalysts which may be employed are alkali hydroxides, especially potassium and cesium hydroxide, alkali silanolates, alkali alcoholates, quaternary ammonium hydroxides such as tetramethylammonium hydroxide, benzyltrimethylammonium butylate, beta-hydroxyethyltrimethylammonium-2-ethylhexoate, quaternary phosphonium hydroxides such as tetra-n-butylphosphonium hydroxide and tri-n-butyl-3-[tris-(trimethylsiloxy)silyl]-n-propyl-phosphonium hydroxide, potassium amide, amines, and mixtures of amines as well as mixtures containing at least two of the basic catalysts cited above.

The amount of catalyst used depends upon which catalyst is used.

In the method of this invention, it is possible to include organosilicon compositions which regulate the chain length of the organo(poly)siloxanes. For example, it is possible to use any organosilicon compositions, which have been or could have been used heretofore, to control chain length in the method for altering the molecular weight of linear or cyclic organo(poly)siloxanes. Examples of such organosilicon compositions which regulate or control the chain length are especially those of the following formula

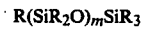

$$R(SiR_2O)_m SiR_3$$

wherein R is the same as above, and m is an integer having a value of from 1 to 50, as well as those of the following formula

$$(R_3Si)_2NH$$

where R is the same as above. Specific examples of such compounds are hexamethyldisiloxane, 1,3-divinyl-1,1,3,3-tetramethyldisiloxane, 1,3-dihydrogen-1,1,3,3-tetramethyldisiloxane and hexamethyldisilazane, as well as those of the following formula

$$R_3SiOH$$

where R is the same as above. Preferred examples of such compositions are trimethylsilanol, dimethylphenylsilanol, methyldiphenylsilanol, triphenylsilanol, dimethylvinylsilanol, methylphenylvinylsilanol, diphenylvinylsilanol and the like.

It is well known in the art that the amount of organosilicon compositions used to control the chain length depends on the desired chain length. The greater the amount of organosilicon composition used to control chain length, the lower the viscosity of the organopolysiloxanes obtained. However, the amount used should be sufficient to at least ensure that the organopolysiloxanes obtained by the method of this invention have an average viscosity of from about 100 to 1 Mio, mPa.s at 25° C.

The catalyst can h=dissolved or suspended in one or several components of the reaction before it is added to the reactor used in the method of this invention. However, it can also be added separately, for example, in the form of a solution or a suspension in an inert liquid.

Examples of suitable inert liquids are unsubstituted or substituted hydrocarbons or mixtures thereof. Examples of unsubstituted hydrocarbons and mixtures thereof are petroleum distillates such as petroleum ether and benzene having various boiling points, pentane, hexane, heptane, octane, their higher homologues and isomeric mixtures; and aromatics such as toluene and xylenes. Examples of substituted hydrocarbons are especially halogenated hydrocarbons such as 1,1,1-trichloroethane and chlorobenzene.

The method of this invention may be carried out at room temperature, i.e., at approximately 20° C.; however, it is preferred that it be performed at higher temperatures. A temperature range of from 80 to 250° C. and especially between 140 and 160° C. is preferred.

The method of this invention may be carried out at atmospheric pressure, i.e., about $10^5$Pa(abs.) or approximately $10^5$Pa(abs.); however, higher or lower pressures may be used as well. When the accompanying products and unreacted starting materials are removed from the reaction mixture by distillation, it is preferred that a pressure lower than $10^5$Pa(abs.) be employed. Pressures between 0.1 and 70,000 Pa(abs.), and especially between 100 and 700 Pa(abs.) are preferred.

Examples of accompanying products and unreacted starting materials which can be removed from the reaction mixture by distillation, are water, solvents and cyclic organosiloxanes. Water is formed during the condensation of silanol groups. Even when no cyclic organosiloxanes are used, these compounds may be generated in the reaction mixture as by-products.

Large quantities of foam are produced when the cited products are removed from the reaction mixture in the conventional reactors, such as the twin-screw kneader of British Pat. No. 1,174,219. Heretofore, the volume in the reactor was kept at a relatively low level in order to keep the foaming reaction mixture from exiting from the reactor. In the method of the present invention, an annular flow is produced within the reactor by stirring which does not result in the formation of foam, or only to a very small extent. Thus, it is possible to fill the reactor to a substantially higher level and to achieve a better space-time-yield ratio. The term "annular flow" is described for example in Perry & Chilton: *Chemical Engineers' Handbook*, 5th Edition, chapter 5, pages 40-42.

The nucleus of the apparatus used in the method of this invention is a horizontal, cylindrical reactor whose length is preferably greater than the inside diameter of the pipe. The reactor is traversed by a lengthwise shaft that is equipped with a stirring blade or with several staggered blades. The blade or blades are located at approximately the same distance from the inside wall of the cylinder, specifically between 30 to 90 percent and more preferably between 50 and 70 percent of the radius of the cylinder. The blade or blades are positioned on the shaft at an angle of between 0 and 45°, and more preferably between 0 and 10°, relative to the shaft. The shaft is driven by a motor. In order to generate an annular flow in the reactive mixture, the rate of rotation of the shaft is selected so that the reactive mixture is forced against the inner wall of the reactor by centrifugal force and a gas-filled space which is substantially free of the reactive mixture is formed in the area through which the blades rotate. The rate of rotation of the shaft, i.e., the centrifugal acceleration necessary to achieve this purpose, can easily be determined visually by using the apparatus described in the following examples.

The directional force is represented by the centrifugal acceleration at the location of the stirring blade that is farthest from the shaft (maximal centrifugal acceleration $b_{max}$), in accordance with the following equation $$b_{max} = 4\pi^2 \cdot r_{max} \gamma^2$$

where $\pi$ represents the sphere factor, $r_{max}$ the maximal distance of the stirrer blade from the shaft in the direction of the reactor's inner wall, and where $\gamma$ stands for the rotational speed of the shaft. In order to achieve an annular flow in the reactive mixture, factors of $b_{max}$ of 70 to 280 m.s$^{-2}$, and preferably from 165 to 220 m.s$^{-2}$ are required. In the case of a stirrer of the type shown in the drawing having a length (3) of 5 cm ($r_{max}$=2.5 cm), this means a rotational speed between 500 and 1,000 rpm, and preferably between 600 and 800 rpm. These are minimal values. Far greater centrifugal acceleration may, of course, be used, although higher operational costs will result. The ratio between the length and the inside diameter of the reactor is between 1:1 and 50:1 and more preferably between 1:1 and 10:1.

It is preferred that the reactor be equipped with a heating jacket. A feed line for the introduction of the reactants and the catalyst is located at one end of the pipe reactor, while a source of vacuum and an outlet for the product are located at the other end. A temperature sensor can be mounted on the inside wall of the reactor.

When the reactor described herein is used in the method of this invention, the advantages described above are achieved; namely, it is possible to suppress the formation of foam in the reactor and to fill the reactor to a higher level when the cylindrical axis of the reactor is inclined between 0° and 10°, and more preferably between 0° and 5° from the horizontal. An increased inclination, i.e., an increased rise as determined from the point of entry of the starting materials into the reactor may, however, be desirable, if it is desired to increase the length of time the reactants remain in the reactor.

In the method of this invention, one or several of the starting materials may be preheated before they enter the reactor. In order to ensure the stability of the product over an extended period of time, it is preferred that the catalyst be removed from or deactivated in the product mixture. Catalysts which are gaseous under the conditions of the reaction can, for example, be largely removed by distillation while they are still in the reactor; whereas, acids and bases can be neutralized.

The reactor used in the following examples consists of a 360 mm long glass tube (6) which has an inside diameter of 60 mm and which is equipped with a heating jacket. The inner volume of the reactor is 1017 cm$^3$. The center of the tube is traversed by a shaft (1) as shown by the drawing, which shaft is driven by an external motor (8). The shaft is equipped with rectangular stirring blades (2), which are 50 mm long (3), and 30 mm wide (4), and which are not inclined relative to the shaft. Relative to each other, the stirring blades are staggered at 90° as shown by the drawing, and are placed at a distance (5) of 5 mm from each other. In the approximate center of the longitudinal axis of the reactor, a temperature sensor (9) extends into the reactive mixture. The reactor is equipped with a feed line (10) for the starting materials at one end and an outlet (11) for the product at the other end of the tube, which also comprises a vacuum connection (12) that communicates with a vacuum pump. The position of the reaction tube is substantially horizontal (inclination angle less than 5° from the horizontal).

The catalysts are prepared in the following manner:

(a) Phosphonitrile chloride in accordance with the procedure described in U.S. Pat. No. 3,839,388.

(b) Tri-n-butyl-3-tris[(trimethylsiloxy)silyl]-n-propyl-phosphonium hydroxide (10 percent by weight solution).

To a two-liter, 3-necked flask equipped with a thermometer, a stirrer and a reflux condenser is added 129 g (0.346 mol) of 3-chloropropyltris-(trimethylsiloxy)-silane and 71 g (0.351 mol) of tri-n-butylphosphine in 1060 ml dimethylformamide, and then with constant stirring, the mixture is heated for 24 hours to 110° C. The dimethylformamide is then distilled off at 10$^{-3}$ hPa(abs.). The residue is dissolved in 700 ml of water and mixed with 70 g of Ag$_2$O. After standing for 24 hours, the mixture is filtered. The filtrate is mixed with 1742 g of a trimethylsiloxy-endblocked dimethylpolysiloxane having a viscosity of 20 mPa.s at 25° C., and thereafter the water is removed from the resultant mixture by being distilled off at 10$^{-3}$hPa(abs.).

EXAMPLE 1

About 15 liters per hour of a mixture consisting of 100 parts by weight (103 parts by volume) of $\alpha,\omega$-dihydroxypolydimethylsiloxane having a viscosity of 140 mm.s$^{-1}$ at 25° C., and 2.9 parts by weight (2.99 parts by volume) of a trimethyl-siloxy-endblocked polydiorganosiloxane having a viscosity of 20 mm$^2$.s at 25° C. are continuously passed through a preheater at a temperature of 160° C. After the mixture has passed through the preheater, 30 ppm (parts per million) based on the preheated mixture of phosphonitrile chloride are added as a 0.75 percent by weight solution in dichloromethane and the resultant mixture is introduced into the reactor. The rotational speed of the stirring device is 700 rpm, its maximal centrifugal acceleration ($b_{max}$) being 134.3 m.s$^{-2}$; while the reactor's inside temperature is maintained at 160° C., while the pressure is adjusted to 10$^{-3}$ hPa (abs.). The average holding time of the mixture in the reactor is 3 minutes. After neutralizing the catalyst with n-butyllithium, an oil is obtained having a viscosity of 110,000 mPa.s. Infrared spectroscopy reveals a residual SiOH content of less than 30 ppm.

EXAMPLE 2

The process of Example 1 is repeated, except that the mixture consists of 45 liters per hour of $\alpha, \omega$-dihydroxypolydimethylsiloxane having a viscosity of 140 mm$^2$.s and 2 ppm of phosphonitrile chloride instead of 15 liters per hour of a mixture containing $\alpha,\omega$-dihydroxypolyorganosiloxane and tri-methylsiloxy-endblocked polydiorganosiloxane and 30 ppm of phosphonitrile chloride. The temperature in the preheater and in the reactor is 145° C., the pressure in the reactor is 79.8 hPa(abs.), and the average holding time in the reactor of the reactive mixture is one minute. The product consists of an oil having a viscosity of 81,500 mPa.s at 25° C.

EXAMPLE 3

The process of Example 1 is repeated, except that instead of adding 30 ppm of phosphonitrile chloride as a 0.75 percent by weight solution in dichloromethane, downstream from the preheater, the addition is made upstream from the preheater and consists of 60 g/hour of a catalyst solution prepared in accordance with (b) above (corresponding to 400 ppm tri-n-butyl-3-tris[(-trimethylsiloxy)silyl]-n-propyl-phosphonium hydroxide, based on the reactive mixture before it enters the preheater). The temperature in the preheater and in the reaction chamber is maintained at 130° C. instead of 160° C. After the resultant mixture exits from the reactor, it is passed through a heat exchanger having an inside temperature of 160° C. in order to remove the catalyst. An oil having a viscosity of 105,000 mPa.s at 25° C. is obtained.

In these examples, the reactors are essentially free of foam formation.

What is claimed is:

1. An improved method for continuously altering the molecular weight of organosilicon compositions containing Si-bonded oxygen in a cylindrical reactor in the presence of a catalyst; the improvement which comprises conducting the reaction in the presence of a homogeneous catalyst in a horizontal cylindrical reactor having a length to inside diameter ratio of from 1:1 to 50:1 and having a stirring mechanism with at least one stirring blade so that the reactive mixture is subjected to a maximal centrifugal acceleration ($b_{max}$) of at least 70 $m.s^{-2}$.

2. The method of claim 1, wherein the reaction is carried out at a pressure of $10^{-3}$ to 1000 hPa(abs.) and at temperatures between 20° and 250° C.

3. The method of claim 1, wherein the reactive mixture is subjected to a maximal centrifugal acceleration ($b_{max}$) of at least 165 $m.s^{-2}$.

4. The method of claim 2, wherein the reactive mixture is subjected to a maximal centrifugal acceleration ($b_{max}$) of at least 165 $m.s^{-2}$.

* * * * *